United States Patent
Fryshman

(10) Patent No.: US 10,147,177 B2
(45) Date of Patent: *Dec. 4, 2018

(54) OBJECT IMAGE RECOGNITION AND INSTANT ACTIVE RESPONSE WITH ENHANCED APPLICATION AND UTILITY

(71) Applicant: Bernard Fryshman, Brooklyn, NY (US)

(72) Inventor: Bernard Fryshman, Brooklyn, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/922,565

(22) Filed: Mar. 15, 2018

(65) Prior Publication Data

US 2018/0204321 A1 Jul. 19, 2018

Related U.S. Application Data

(63) Continuation of application No. 15/802,814, filed on Nov. 3, 2017, now Pat. No. 9,965,850, which is a (Continued)

(51) Int. Cl.
*G06T 7/00* (2017.01)
*A01H 1/02* (2006.01)
(Continued)

(52) U.S. Cl.
CPC .......... *G06T 7/0008* (2013.01); *A01H 1/025* (2013.01); *A01M 1/026* (2013.01); *A01M 1/06* (2013.01); *A01M 1/14* (2013.01); *A01M 1/20* (2013.01); *A01M 1/2094* (2013.01); *A01M 1/22* (2013.01); *A01M 1/226* (2013.01); *A01M 3/005* (2013.01); *A01M 3/007* (2013.01); *A01M 5/02* (2013.01); *A01M 5/04* (2013.01); *A01M 7/00* (2013.01); *A01M 21/043* (2013.01); *A01M 99/00* (2013.01); *B64C 39/024* (2013.01); *B64D 1/18* (2013.01); *B64D 47/08* (2013.01); *G06K 9/00* (2013.01); *G06K 9/6256* (2013.01);
(Continued)

(58) Field of Classification Search
CPC combination set(s) only.
See application file for complete search history.

(56) References Cited

U.S. PATENT DOCUMENTS 4,094,088 A 6/1978 Harrell
4,569,153 A * 2/1986 Szilagyi ................ A01M 21/00
47/23.2

(Continued)

OTHER PUBLICATIONS

International Search Report received for PCT Patent Application No. PCT/US2017/32154, dated Jun. 6, 2017, 4 pages.
(Continued)

*Primary Examiner* — Anand P Bhatnagar
(74) *Attorney, Agent, or Firm* — Amster, Rothstein & Ebenstein LLP

(57) ABSTRACT

A device for detecting an offending object such as weeds or insects, and addressing the offending object by removing or marking the same. The device has image acquisition and image recognition systems that captures images of plants and automatically responds by way of an action when a weed or insect is identified. The action head may grip the offending object or release a substance such a herbicide to eliminate a weed.

10 Claims, 5 Drawing Sheets

Related U.S. Application Data continuation-in-part of application No. 15/654,390, filed on Jul. 19, 2017, now Pat. No. 9,852,362, which is a continuation-in-part of application No. 15/425,079, filed on Feb. 6, 2017, now Pat. No. 9,811,764, which is a continuation of application No. 15/153,621, filed on May 12, 2016, now Pat. No. 9,563,945, which is a continuation-in-part of application No. 14/733,044, filed on Jun. 8, 2015, now Pat. No. 9,381,646, which is a continuation-in-part of application No. 14/505,430, filed on Oct. 2, 2014, now Pat. No. 9,053,528, which is a continuation-in-part of application No. 13/542,416, filed on Jul. 5, 2012, now Pat. No. 8,855,374.

(60) Provisional application No. 62/183,591, filed on Jun. 23, 2015, provisional application No. 62/551,345, filed on Aug. 29, 2017.

(51) Int. Cl.

| | | |
|---|---|---|
| *B64D 1/18* | (2006.01) | |
| *B64C 39/02* | (2006.01) | |
| *H04N 7/18* | (2006.01) | |
| *A01M 7/00* | (2006.01) | |
| *G06K 9/62* | (2006.01) | |
| *H04N 5/225* | (2006.01) | |
| *G06K 9/00* | (2006.01) | |
| *A01M 3/00* | (2006.01) | |
| *A01M 1/22* | (2006.01) | |
| *A01M 1/20* | (2006.01) | |
| *A01M 1/14* | (2006.01) | |
| *A01M 1/06* | (2006.01) | |
| *A01M 1/02* | (2006.01) | |
| *A01M 5/04* | (2006.01) | |
| *A01M 5/02* | (2006.01) | |
| *A01M 99/00* | (2006.01) | |
| *B64D 47/08* | (2006.01) | |
| *G06T 7/90* | (2017.01) | |
| *G06T 7/62* | (2017.01) | |
| *A01M 21/04* | (2006.01) | |

(52) U.S. Cl.
CPC .......... *G06K 9/6267* (2013.01); *G06T 7/0004* (2013.01); *G06T 7/0014* (2013.01); *G06T 7/62* (2017.01); *G06T 7/90* (2017.01); *H04N 5/2252* (2013.01); *H04N 5/2253* (2013.01); *H04N 7/185* (2013.01); *B64C 2201/027* (2013.01); *B64C 2201/12* (2013.01); *G06K 2209/17* (2013.01); *G06T 2207/10024* (2013.01); *G06T 2207/10032* (2013.01); *G06T 2207/10056* (2013.01); *G06T 2207/20081* (2013.01); *G06T 2207/30128* (2013.01); *H04N 5/225* (2013.01); *Y02A 50/375* (2018.01); *Y10S 901/01* (2013.01); *Y10S 901/09* (2013.01); *Y10S 901/40* (2013.01); *Y10S 901/41* (2013.01)

(56) References Cited

U.S. PATENT DOCUMENTS

| | | | | |
|---|---|---|---|---|
| 4,575,304 | A * | 3/1986 | Nakagawa | B25J 9/1015 414/730 |
| 5,927,603 | A * | 7/1999 | McNabb | A01G 25/092 239/63 |
| 5,957,933 | A * | 9/1999 | Yanof | A61B 90/11 606/129 |
| 6,508,033 | B2 | 1/2003 | Hessel et al. | |
| 6,671,582 | B1 * | 12/2003 | Hanley | A01B 51/02 250/339.11 |
| 7,315,794 | B1 * | 1/2008 | Willis | G01B 11/024 702/155 |
| 7,747,351 | B2 * | 6/2010 | Tsusaka | B25J 9/0003 177/25.11 |
| 7,765,780 | B2 | 8/2010 | Koselka et al. | |
| 7,830,504 | B2 | 11/2010 | Deppermann et al. | |
| 7,854,108 | B2 * | 12/2010 | Koselka | A01D 46/30 56/10.2 A |
| 8,381,501 | B2 * | 2/2013 | Koselka | A01D 46/30 56/10.2 A |
| 8,391,550 | B2 | 3/2013 | Pachys | |
| 8,452,449 | B2 * | 5/2013 | Iida | B25J 9/1638 156/750 |
| 9,545,723 | B2 * | 1/2017 | Chang | B25J 9/1664 |
| 2001/0036295 | A1 | 11/2001 | Hendrickson et al. | |
| 2005/0126144 | A1 | 6/2005 | Koselka et al. | |
| 2005/0275060 | A1 * | 12/2005 | Dokumaci | H01L 21/31144 257/510 |
| 2006/0079067 | A1 * | 4/2006 | Shin | H01L 21/0274 438/401 |
| 2006/0199379 | A1 * | 9/2006 | Yeh | H01L 21/31144 438/638 |
| 2006/0211178 | A1 * | 9/2006 | Kim | H01L 27/10852 438/129 |
| 2011/0049718 | A1 * | 3/2011 | Matsumoto | C23C 16/40 257/751 |
| 2011/0137456 | A1 * | 6/2011 | Koselka | A01D 46/30 700/245 |
| 2011/0211733 | A1 * | 9/2011 | Schwarz | A01B 41/06 382/110 |
| 2013/0204437 | A1 * | 8/2013 | Koselka | A01D 46/30 700/259 |
| 2016/0368135 | A1 * | 12/2016 | Tadayon | B25J 5/02 |

OTHER PUBLICATIONS

Written Opinion received for PCT Patent Application No. PCT/US2017/32154, dated Jun. 6, 2017, 4 pages.

* cited by examiner

OBJECT IMAGE RECOGNITION AND INSTANT ACTIVE RESPONSE WITH ENHANCED APPLICATION AND UTILITY

FIELD OF THE INVENTION

The current invention relates to the field of automated review and response, more specifically to a novel method and apparatus for reviewing images to detect changes from a previous version and automatically marking any detected changes.

BACKGROUND OF THE INVENTION

The decreased use of pesticides on the one hand and the decreased effectiveness of those which are in use has resulted in a disturbing proliferation of insects in food and in the home. Moreover, insects or other invading species frequently infest orchards or similar crops.

The invention described herein makes it possible to detect and immediately dispose of thrips, mites and aphids, among other insects, including those invisible to the untrained and unpracticed eye.

Many such insects are very difficult to dislodge by washing and are resistant to pesticides. Large scale efforts such as by heating often harm the food or other material to be cleansed.

SUMMARY OF THE INVENTION

The invention disclosed herein is a computer image analysis system, which magnifies an image of a substrate to be checked for bugs or other small objects and is trained to recognize various bugs commonly associated with such substrates to be checked. If a bug is identified any of various action steps are taken in different embodiments of the invention, including removing the bug by way of an action head associated with the imaging device. In other embodiments of the invention, the system is positioned on a movable platform to scan a wide area for offending objects and/or to perform mitigation actions once an offending object is detected.

Still in other embodiments of the invention, the system is configured to detect differences between a secondary image and a reference images. That is, the system is configured to review images and compare the reviewed images to a previously captured image of the same area to detect differences between the two. In the event that a difference is detected, an action head is automatically deployed to dispense marking material in the image area or in the proximity of the image area where the difference was detected.

DETAILED DESCRIPTION OF THE INVENTION

Embodiments of the present invention will now be described with reference to the above-identified figures. However, the drawings and the description herein of the invention are not intended to limit the scope of the invention. It will be understood that various modifications of the present description of the invention are possible without departing from the spirit of the invention. Also, features or steps described herein may be omitted, additional steps or features may be included, and/or features or steps described herein may be combined in a manner different from the specific combinations recited herein without departing from the spirit of the invention, all as understood by those of skill in the art.

In one preferred embodiment, a lens is used to point at a leaf of lettuce and capture an enlarged image thereof via an image capturing device. The image may be stored in digital memory for later analysis or it may be analyzed in real time. In either case, the image is sent to a processor that is trained to recognize the general characteristics and color of the lettuce, and which is also trained to recognize physical characteristics and features of insects typically found on lettuce. The image is magnified so that the presence of the insect, even if well hidden, will be identified by comparison with a library of insects stored in memory. In one embodiment, the processor does not positively identify a bug or other identifiable foreign object, but it may recognize the object as foreign. For instance, a processor may contain parameters of acceptable color values or hues for a specific substrate and if an object is outside of such parameters—software running on the processor determines the object as "foreign."

The identification of the insect will immediately trigger a response in an action head which is attached to the lens housing and is capable of moving to the insect position, and removing or destroying the insect automatically. In another embodiment of the invention, rather than removing an observed insect—an action head grips the piece of lettuce and discards it.

Figure 1:
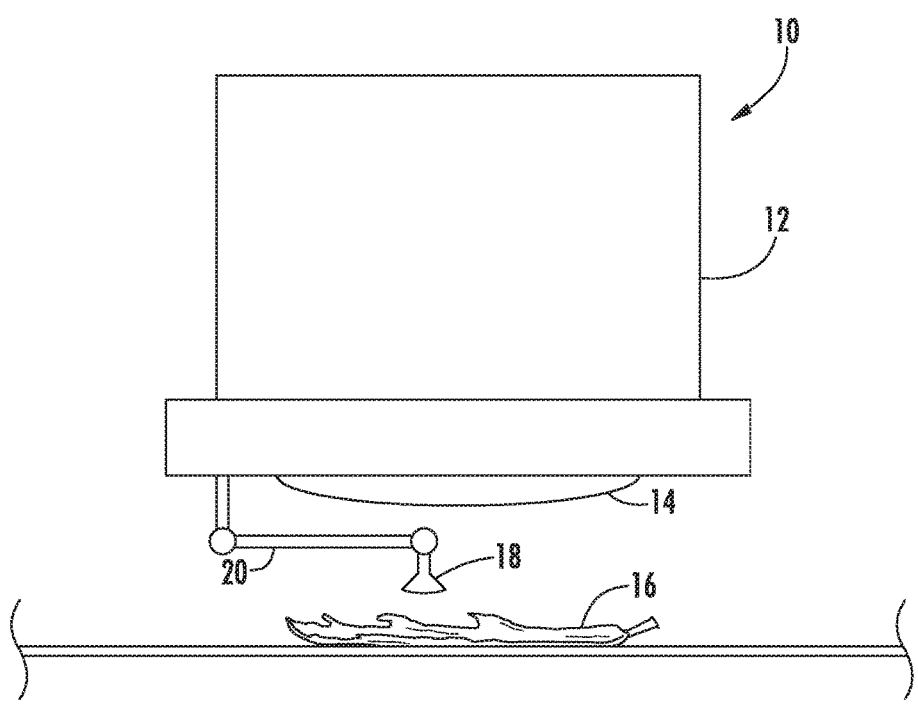
FIG. 1 shows a schematic side view of a scanning device disposed above a substrate to be checked according to an embodiment of the invention.

FIG. 1 shows a scanning device having a casing 12, which houses an image recognition system. A downward facing microscope, lens 14 or any such image capturing device and magnification device is located at a bottom portion of the scanning device. As shown, the lens 14 is directed at a substrate 16, such as, for example, a piece of lettuce. The lens magnifies a segment of a substrate to be checked and it feeds captured images to an image recognition system for image analysis. Images may be stored on a digital storage medium, among other storage systems or media.

It will be understood by those of ordinary skill in that the device 10 may be provided with a plurality of differently powered lenses which may be automatically adjusted when greater focusing ability is needed and any of different image capturing devices may be utilized, such as for example, a camera or a video camera, or an array thereof. It will also be understood that the image recognition system need not be housed within the casing 12 of the device—but rather the image recognition software may be provided at a location that is distant from the image-capturing device. In such embodiment, an image-capturing device (e.g. a microscope lens coupled to an image capturing system) is utilized to capture images. The images are then sent by a wired or wireless connection to an image classifier.

FIG. 1 shows an action head 18, which is provided at the distal end of a movable arm 20. The action head may be equipped with one or more instruments, such as a gripping device and/or a suctioning device. In another embodiment of the invention, the action head is provided with a heating element or such similar heat source—which can destroy a bug or a segment of lettuce when it is brought into direct contact therewith.

In one embodiment of the invention, the device 10 housing the lens 14 and action head 18 is a handheld unit, which may be manually or automatically moved across a stationary substrate such as a leaf of lettuce. In another embodiment the device 10 is mounted on a stationary support structure and a conveyor belt positioned below the device delivers items to be scanned below the microscope lens of the device. Still in other embodiments of the invention, the device is mounted to a linear motion track and it incrementally moves (for instance by incremental movements of a rack and pinion wheel controlled by a computer) across a substrate to be searched. In one embodiment, the device 10 may be used for purposes of "surveillance." In this embodiment, the device is mounted in a fixed position. When an offending object (such as an insect) enters the field of vision of the lens and is recognized as such by the image recognition system—a command is sent to activate the action head 18 to eliminate and/or neutralize the offending object. It will be understood that as an alternative to eliminating and/or neutralizing an offending object, the device could mark the offending object for subsequent removal or remedial action. In embodiments, device 10 may be a drone, which may be a remotely controlled and/or autonomously controlled vehicle (e.g., aircraft, ground vehicle). For example, an autonomous vehicle may operated accordingly to pre-programmed rules, such as navigation directions (e.g., coordinates or street directions), and/or logical rules to govern operation, such as obstacle avoidance rules and/or task execution rules (e.g., using a scanning or imaging device to assess various subjects), to name a few.

It will be further understood that the moveable arm described herein may be its own detached unit, but which operates under the control of the software, which software may be stored in memory on the device 10 and configured to run on one or more processors, or which software may be remotely located, such as on a remote server accessible via a data communication signals and/or data networks. An exemplary device control system is described herein with respect to FIG. 4.

In an embodiment of the invention, action head 18 is mounted on exterior surface of a device such as a drone, a vehicle, or the like. In other embodiments, action head 18 is attached to the distal end of a movable arm. It will be understood that a movable arm may be any of various structures such as, for example, one or more linear guide tracks, rack and pinion systems or such similar relative motion mechanism for supporting and moving an action head is within the teaching of the invention. The arm is movable in any of various directions by way of ball joints, linear motion tracks or other such similar movement systems. When a bug or other offending object is detected by the image recognition system, the software is programmed to send a signal to the moveable arm. The moveable arm is then controlled by a software application and directed to the located bug. The action head is deployed to either destroy the bug as described above or to suction it off of the substrate. In one embodiment of the invention, rather than directing the action head to a specific location—the moveable arm is directed to push the piece of lettuce (or other substrate) away, thereby discarding the same or removing it from a batch.

The computer used to control operations, execute routines and store data may comprise at least one or more processors and memory storage devices. The computer also may receive a number of inputs and outputs for communicating information externally.

It will be understood that the computer which operated the device may operate under the control of an operating system and software applications, components and programs that execute the routines and systems described herein. In general, the routines executed to implement the embodiments of the invention, whether implemented as part of an operating system or a specific application, component, program, object, module or sequence of instructions will be referred to herein as "the system", or "software". The software controls the image acquisition, image storage, image analysis and movements of the arm, action head and/or the movement of the device along a track.

It will be understood by those of ordinary skill in the art that the inventive device is an apparatus having image capturing capabilities and image recognition capabilities coupled with software that is programmed to determine whether or not an object in an image field is an offending object. An "offending object" herein is any physical, identifiable structure or shape that is targeted for action. Examples of offending objects may include, but are not limited to, insects, dirt, mold growth, plant features, product imperfections etc. The device is programmed to take an action once an offending object is detected. "Action" refers to any remedial steps taken by the device to eliminate or otherwise address the offending object. For example, in one embodiment of the invention, the action head 18 of device 10 advances to a location of an offending object and it records the spatial coordinates of the same. The coordinates are stored for later treatment and or elimination.

Figure 2:
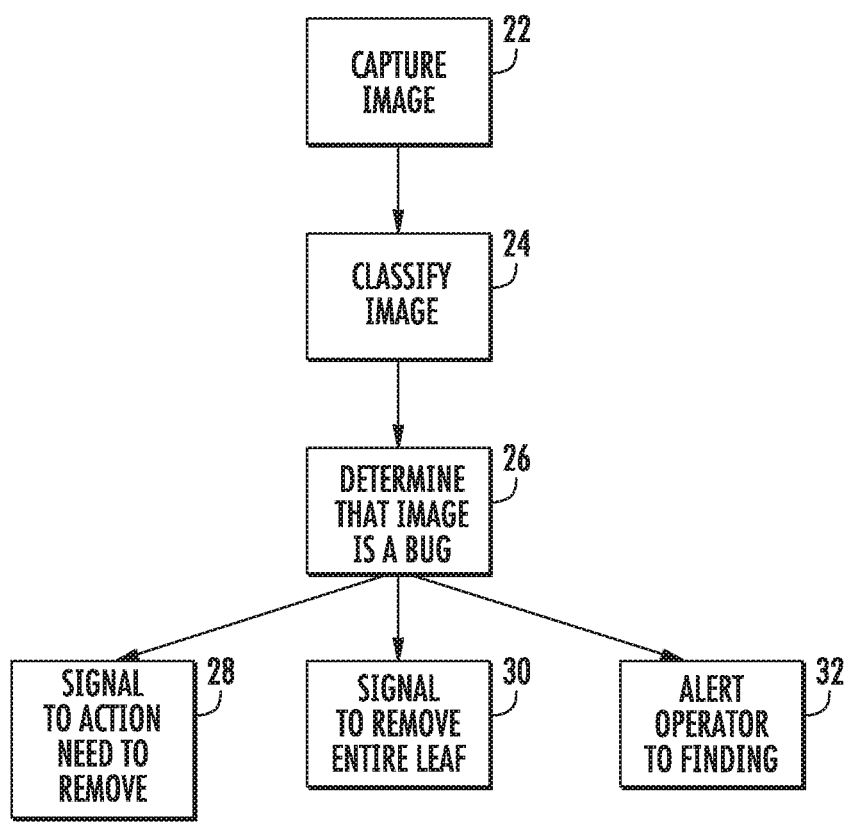
FIG. 2 is a flow chart showing software processing steps according to an embodiment of the invention.

FIG. 2 shows a number of processing steps performed by the software in an exemplary embodiment of the invention.

The device is initiated and begins capturing images 22. The images are sent to an image recognition system which classifies various images 24. The classifier may be an algorithmic classifier or a neural network system. The image recognition system is trained to recognize morphological/physical characteristics of bugs or other objects to be detected. The image recognition may also be trained to detect pixel concentrations which may indicate the presence of bug or other objects of interest.

If an image is determined to be a bug 26, then the software performs further processing steps.

In one embodiment, the software sends a signal to the moveable arm 28, which directs the action head to the location of the bug to remove the same according to the teachings described above.

In another embodiment of the invention, the software sends a signal to the moveable arm to push aside the item 30 upon which the bug was detected.

Still in another embodiment of the invention, upon detecting a bug, the software sends or sounds an alert to a human operator 32. The human operator may intervene to remove the bug or the item.

In another preferred embodiment, the device is designed to deal with only one kind of insect on one kind of food or other material. A single kind of action suitable for the situation will be built into this device.

Extension is obvious to a more sophisticated device with software taught to deal with many different kinds of foods and materials, to recognize a range of different insects or objects, and different means of removing the insect, including vacuum, a glue head, an electrical charge, freezing, heat, or even a drop of powerful insecticide. Powerful pesticides sprayed or deposited over a large area is harmful, but a targeted drop on the insect itself will dispatch the insect and not affect the surrounding atmosphere.

In another embodiment, there will be an array of lenses and response heads so that a sheet being inspected for bed bugs can be continuously passed under the array.

In another embodiment of the invention the inventive system may be used to remove offending objects, such as bugs, from a fluid. In one embodiment, an image capturing device is fixed above a channel of flowing liquid. The device may comprise an array of image capturing devices or lenses suspended above a channel or similar fluid stream. It will be understood that in an embodiment of the invention, the action head may be a vacuum head or suction head such that when the image recognition system detects a presence of an offending object, the software sends a command to the action head to vacuum an area of fluid in the vicinity of the offending object. The vacuum head or suction head will draw in the offending object, and possibly, some of the surrounding fluid and discard the same.

The invention may be used in any of various environments in which subtle changes need to be detected and then acted on. For example, the beginning of a disease affecting trees or other plants and its subsequent spread is often the result of an insect, beetle or bug penetrating the bark or other surface and destroying the structure from within. Detecting a presence of a specific kind of invader is virtually impossible if it requires a human observer's continued close observation. The instant invention can be deployed in a manner which detects and acts whenever an invader is detected on the surface. For example, the software may be trained to detect specific bugs or locusts. Once detected, the software sends a command to spray an offending substance or a pesticide.

In another embodiment of the invention, the software is programmed to detect swarms of bugs or flying objects—irrespective of the type of bugs or objects. In one example, the software is trained to detect a plurality of distinct moving objects within an area of interest. Once a threshold number of moving objects (e.g. >10) is detected, the software will confirm a presence of a swarm and it will automatically send instructions to the action head to address the swarm. In one embodiment, the action head will spray a mist of water vapor or insecticide, smoke laced with insecticide, repellant or similar offending substances. Alternatively, the device will sound an alarm to disperse the swarm.

The invention can be modified to recognize the sign of incipient disease on the skin of a human being at a size almost invisible to the human eye. It is evident that the principles of the invention can be readily applied to other areas where detection, recognition, and action of a flaw, intrusion, or incipient flaw at a stage where it is barely visible.

Depending on the specific use, it is obvious that the invention can be associated with a variety of platforms, both mobile and stationary. For example, the image capturing lens and action head may be mounted to a movement mechanism such as a linear guide track, a pulley system, a rack and pinion or any such similar movement mechanisms. Alternatively, the device may be attached to or embedded within a drone, hovercraft, aircraft or similar dirigible. (Mechanical devices/mechanisms for moving the device referred to as "movable platforms" herein.) In the embodiment whereby the device is mounted to a movement mechanism, the software may be programmed to move the device in any of various pre-determined or random movements. In an embodiment of the invention, once an offending object is detected, the software sends a command to interrupt movement of the device and deploy the action head to execute remedial actions.

Control of any of the above mobile or active platforms envisioned above can be implemented in a variety of ways, including voice recognition.

It is obvious that the insect image recognition and instant active response device, as well as any attendant platform or support can be supplied with energy in a variety of ways, including batteries, solar, electromagnetic and hard wires, among others.

The instant invention is not limited to any specific materials of construction or size, and is readily modified by change in programmed recognition patterns to react to different insects, insect parts, plants, plant parts, and in one preferred embodiment, to detect extremely small predictable defects or imperfections, among others, in the manufacturing process or in manufactured products.

In this latter use, it is obvious that more than one device can be connected to work in tandem, or in any manner called for by the situation.

In one preferred embodiment, a device in accordance with the invention is furnished with assisted illumination to extend its use at night, through the use of light and infrared, among others. To extend its use further, x-ray and other surface penetrating radiation can be attached to the platform or to the device itself.

It is obvious to someone skilled in the art that the image recognition and instant response feature can be incorporated into or provided on the platform.

In one preferred embodiment, a robot platform or movable platform may be provided with an image magnification device to magnify an image of an area, segment and/or substrate to detect objects it is trained to detect.

It will be understood that in addition to observing and capturing images, the robot or movable platform may be programmed to provide an active response to remove, mitigate and/or react to various conditions. Any of a variety of actions steps may be deployed by the robot such as, but not limited to, sending an alert or an update, and/or expelling a spray or substance such as pesticide, vapor or smoke. For example, in embodiments of the invention a movable platform such as a robot, vehicle, or drone is utilized to travel about a field, orchard or forest and obtain images of plants and/or trees growing therein. The software detects any of various conditions associated with plants and/or trees and is trained to react accordingly. In one embodiment, the device is trained to detect boring insects (e.g. Emerald Ash Borers) by recognizing physical features such as appearance, color, size, shape etc. Additionally or alternatively, the device detects holes in plants or trees created by such insects. The device then automatically responds by directing the action arm to the detected insect or its entry hole. For example, in one embodiment, the device directs the action arm to an entry hole formed by boring insects and releases a blast of white paint or similar marking material to mark the tree for removal or for remedial treatment.

In a further implementation of the invention, the device is programmed to provide an instant response which results in recognition and capture instead of recognition and reject. That is, objects, such as insects, which are of interest instead of being offending, can be trapped and captured with the same device, using only an obvious modification. That is, rather than dispersing or deflecting an object of interest, the software sends a signal to the mechanical arm to capture and maintain the object of interest.

The inventive device may be deployed for use in quality control activities. In this embodiment, the device may be trained to recognize qualitatively acceptable objects and those that do not meet acceptable criteria (or "defective objects"). The software is programmed to employ an action head to capture defective objects. Acceptable criteria may be any of size criteria, shape criteria or such similar metrics calculated by the software or algorithmic classifier. In other embodiments, acceptable criteria may be based on color criteria, pixel counts, pixel saturation or any such similar image criteria the software and image recognition/analysis software is programmed to analyze.

It is obvious to anyone skilled in the art that the invention can be modified to be used as a stand-alone, hand held device, or fixed in place with items to be inspected passing through. It is also evident that lens/image capture device and action heads can be in a circular or other convenient pattern, and on both sides of the material, as on both sides of a sheet.

In one preferred embodiment, the invention is attached to a drone which is programmed to move up and down, and all around a tree periodically, subsequently to move on to other trees. This will enable the instant invention to protect forests, orchards and plantations against invasive species. Drones can be programmed to travel in certain sectors of a forest or orchard, around a periphery or in any pattern as designated by an operator to capture images in the area below it and instantly react.

A drone can also be programmed to remain stationary, detecting and protecting against the arrival of an expected invasive species for which it has been trained. Similarly, attaching the device to a robot enables the protection against land based invasive species.

In each case, the proliferation of robots and drones, as well as other platforms, extends the use and effectiveness of the device. Included in such other platforms are hovercrafts, extendable legs and floatable devices among others known to those skilled in the art.

Figure 3:
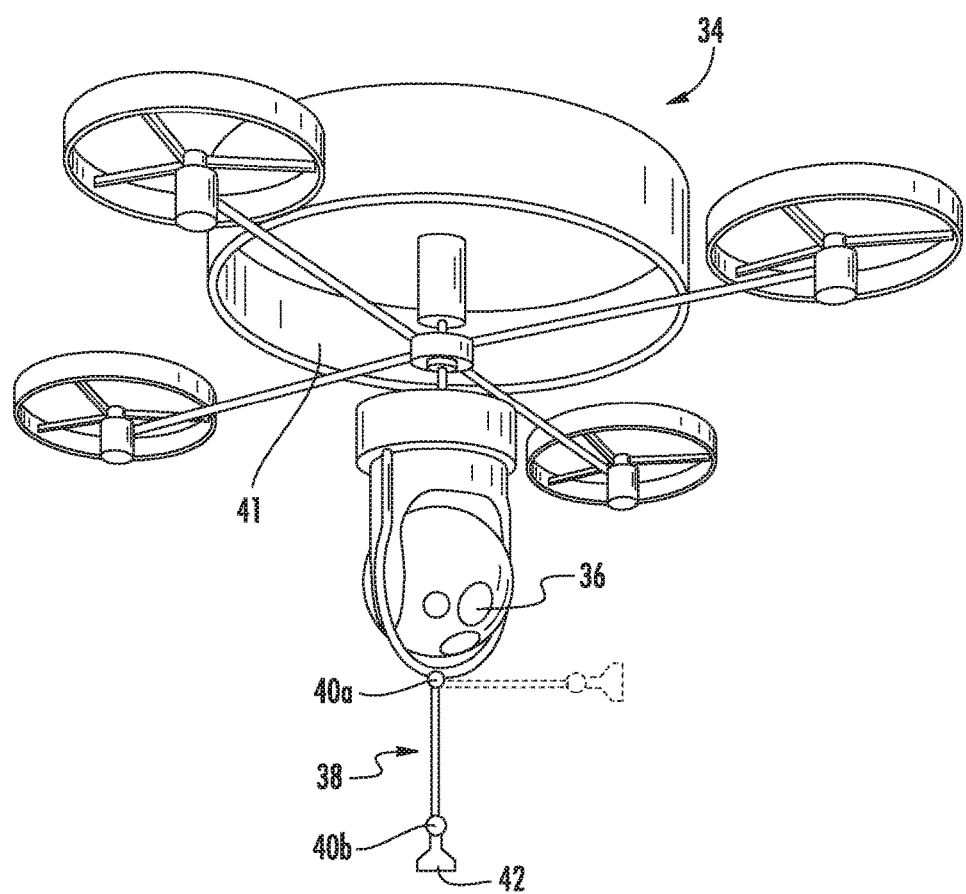
FIG. 3 shows a side perspective view of a scanning device incorporated with a drone according to an embodiment of the invention.

FIG. 3 shows a drone 34 used to capture images and provide an active response according to an embodiment of the invention. Drone 34 has an image capturing device for capturing images of areas to be analyzed. For example, as shown, drone 34 has a lens 36 which is part of a camera or video camera. In a preferred embodiment, the image capturing device is housed in a movable and/or rotatable housing. The lens 36 captures images, which are then analyzed by the image analysis software. The image analysis software may be located in a computer residing in the drone 34 or images may be sent via wire or wireless communication to a computer at another location.

An action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body 41 of the drone, but it could be rotated around joint 40a to a 90° angle.

An action head 42 is shown positioned at the terminal end of action arm 38. The software is configured to direct action head 42 in the direction of a detected offending object and to automatically initiate remedial actions. For example, action head 42 is activated to expel any of various substances described above in response to a command from the software. A tank or similar storage reservoir within the drone stores substances to be dispersed or dispensed from the drone.

In another embodiment of the invention, drone 34 is used to capture images of plants or features of plants and to disperse pollen in response to such detection. In embodiments of the invention, the system detects images of plants such as flowers and trees to determine whether or not the plant is a flowering plant adapted for receiving pollen. Additionally or alternatively, the system detects plant object or features that are adapted to receiving pollen. Upon detection of such plants and/or upon the detection of reproductive features of flowering plants—the drone automatically dispenses pollen. In embodiments of the invention, the pollen is directed to the approximate location of detected flowering plants, but in other embodiments, the pollen is directed to an area proximate to a detected flower or reproductive feature.

In embodiments of the invention, an image capturing mechanism is used to capture images of plants, trees or other vegetation and image analysis software is utilized to detect objects consistent with flowering plants. As will be understood by those of ordinary skill in the art, the image analysis software may be located in a computer residing in the drone 34 or images may be sent via wire or wireless communication to a computer at a remote location. The image analysis software determines whether or not a plant is one that is adapted to receive pollen and/or whether or not a plant feature is an organ that is adapted to receive pollen (such as a pistil).

In embodiments of the invention, the drone 34 may be directly controlled by a human operator, whereas, in other embodiments the drone is controlled by one or more computers. The drone 34 flies over areas of vegetation and its image capturing system scans the terrain below. In embodiments of the invention, the image analysis system is trained to detect specific plants for purposes of pollination. In other embodiments, the image analysis system is additionally or alternatively trained to detect specific plant features that are adapted for receiving pollen.

In embodiments of the invention, once a particular plant-type is detected, the system is programmed to release pollen in the vicinity of such detected plants. That is, once a plant of interest is detected, the software sends a command to the drone to navigate toward such plants and to release pollen.

In other embodiments of the invention, the system is programmed to detect specific plant features, like pistils. Once a pistil is detected, the program sends a command to an action arm to release pollen in the direction of the detected pistil. Action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body of the drone, but it could be incrementally rotated around joint 40a to a 90° angle in order to more accurately point the action head 42 in the direction of a pistil.

Action head 42, shown positioned at the terminal end of action arm 38, is provided with a nozzle or such similar spout for releasing a cloud, mist or similar stream of pollen. The software is configured to direct action head 42 in the direction of a flower to be pollinated and automatically expel pollen in the direction of the plant of interest, flower of interest, or plant feature of interest. A tank or similar reservoir within the drone stores substances to be dispersed or dispensed from the drone.

In one exemplary implementation of the invention, the system is programmed to detect features associated with almond trees. In this embodiment, once the software confirms a presence of an almond tree, it will automatically send instructions to navigate the drone 34 to an area proximate to the almond tree and subsequently send instructions to the action head 42 to release pollen. In one embodiment, the software is trained to identify flowers on a almond trees and to disperse pollen on or near respective flowers. In other embodiments, the system is trained to detect respective reproductive features on flowers of the almond tree (such as pistils) and the action arm is instructed to direct the action head 42 toward the reproductive features. Once the action head is properly oriented, a command is sent to expel a spray or mist of pollen.

In a preferred embodiment of the invention, the software is trained to recognize a specific pistil and initiate a dispersal of pollen that is specific to the pistil of interest. In another embodiment of the invention, reservoirs of different pollen types are provided on the drone or similar movable device. The software is trained to recognize and detect a variety of different flowers/pistils (associated with different flowers or flower types) and disperse a pollen type that corresponds to the detected pistil.

It will be understood by those of ordinary skill in the art that drone 34 or a similar aircraft, hovercraft or dirigible having an image capturing device in communication with an image recognition system may be used to detect and monitor any of various conditions and instantly react by dispersing any of various substances or performing other actions via an associated action head. For example, a device may be programmed to detect plant conditions or soil conditions (e.g. using color properties thereof) and to automatically disperse water or nutrients to the detected areas when a dry soil condition or an unhealthy plant condition is detected. In other embodiments, a device may be programmed to detect fires. For example, a drone may be programmed to fly over a forested area and detect visual indicia of smoke or fire. Additionally or alternatively, the device may have a heat sensor to detect fires. Once a fire is detected, the device is programmed to navigate into proximity of the fire and automatically disperse fire retardants such as chemicals or water.

It will be understood that the computer which operated the device may operate under the control of an operating system and software applications, components and programs that execute the routines and systems described herein. In general, the routines executed to implement the embodiments of the invention, whether implemented as part of an operating system or a specific application, component, program, object, module or sequence of instructions will be referred to herein as "the system", or "software". The software controls the image acquisition, image storage, image analysis and movements of the arm, action head and/or the movement of the device along a track or other movement mechanism.

Figure 4:
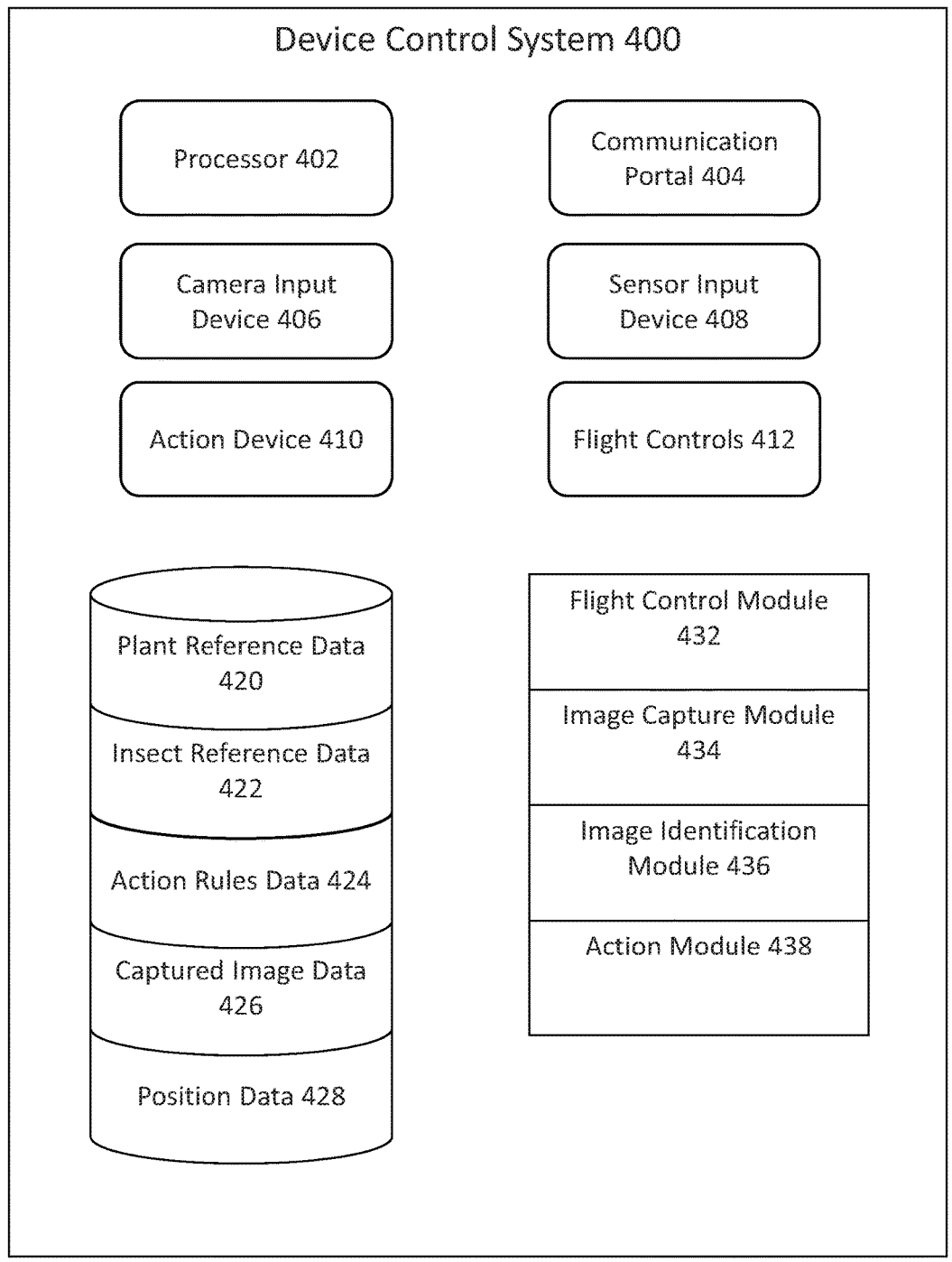
FIG. 4 is a schematic diagram of an exemplary device control system according to an embodiment of the invention.

FIG. 4 is a schematic diagram of an exemplary device control system 400. The device control system may comprise a computer system comprising one or more computers. The device control system may govern operation of an imaging and/or image evaluation device, as may be employed by an imaging drone as described herein. In embodiments, certain components of the device control system 400 may be located on-board the device, such as on or within a drone, or remotely, such as at a remote computer system, which may be accessible via a data network. For example, the image identification module 436 and/or action module 438 may be located remotely, e.g., on one or more servers. Image data may be uploaded (via physical connection of memory storage devices and/or wirelessly) to the image identification module 436 for evaluation. In embodiments, action instructions may be transmitted by an action module 438 to one or more drones for execution.

The device control system 400 may comprise hardware, such as one or more processors 402, a communication portal 404, one or more camera input devices 406, one or more sensor input devices 408 (e.g., scanners, range finders, position sensors (e.g., GPS receivers, altitude sensors, to name a few), action device 410 (e.g., action head and/or movable arm, as described herein), and/or flight controls 412. Flight controls 412 can include thrusters, engines, motors, turbines, fans, rotors, propellers, thrust vectoring control surfaces, aerodynamic control surfaces, and/or actuators and/or servo motors to move such hardware components. In embodiments, a drone can include wheels, treads and tracks, or other ground propulsion systems, including motors. In embodiments, the drone can be designed to float and thus may include floatation devices (e.g., pontoons) or buoyant exterior components of the drone, as well as water propulsion systems.

The device control system 400 may further comprise non-transitory computer-readable memory (e.g., local and/or remote), which may store and/or access data, e.g., in one or more databases. Such data can include plant reference data 420, insect reference data 422, action rules data 424, captured image data 426 or other sensor data, and/or position data 428, as described herein. The device control system 400 may also include one or more software module stored in the memory and configured to execute machine-readable instructions to perform one or more processes. Such modules can include a flight control module 432, image capture module 434, image identification module 436, and/or action module 438. The processes and functions described with respect to each module may be performed by one or more other modules, such as other modules described herein or additional modules.

The communications portal 404 may handle, process, support, and/or perform wired and/or wireless communications, such as transmitting and/or receiving data (e.g., data packets). In embodiments, transmission described with respect to a single data packet may comprise a plurality of data packets. Data packets may be discrete electronic units of data. In other embodiments, transmissions may comprise non-discrete signals, such as data streams. Transmissions described with respect to data packets may also comprise data transmissions via other communications mechanisms known in the art, such as data streams. Communications portal 404 can comprise hardware (e.g., hardware for wired and/or wireless connections, such as communications chipsets, communications interfaces, and/or communications antennas, to name a few) and/or software.

Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few.

Wireless connections may include cellular or cellular data connections and protocols (e.g., digital cellular, PCS, CDPD, GPRS, EDGE, CDMA2000, 1×RTT, Ev-DO, HSPA, UMTS, 3G, 4G, 5G, and/or LTE, to name a few), Bluetooth, Bluetooth Low Energy, Wi-Fi, radio, satellite, infrared connections, ZigBee communication protocols, to name a few.

Communications interface hardware and/or software, which may be used to communicate over wired and/or wireless connections, may comprise Ethernet interfaces (e.g., supporting a TCP/IP stack), X.25 interfaces, T1 interfaces, and/or antennas, to name a few.

Turning to the data that the device control system 400 may store and/or access, plant reference data 420 can include one or more images of each of a plurality of species for image comparison purposes and/or an identifier or database association to indicate the respective species associated with each image. In embodiments, the plant reference data can include images of plant parts, such as a pistil, petal, or leaf, to name a few. Plant reference data can also include growing condition data, which may be coupled with GPS data of captured images to narrow the number of reference images that are likely to produce a match. Growing condition data can include any of water availability, soil type, temperature information (e.g., temperature ranges), climate, geographic location information, to name a few.

Insect reference data 422 can include one or more images of insects of various species or insect components (e.g., wings) and an indicator or reference to associate each image with its respective species. Insect reference data may include size information (e.g., cross-sectional measurements, measurements of body components, such as body segments, antennas, legs), body information (e.g., number of body segments, number of antenna), color information, geographic information (e.g., indicating where the insect is likely to be found), habitat information (e.g., indicating habitats in which the insect is likely to be found, such as they type of crops, type of terrain, temperatures), and/or food source information.

Action rules data 424 can comprise rules to control an action device 410 (e.g., to control movement and/or usage of the action device 410) and/or logical rules to govern when to use the action device 410.

Captured image data 426 can comprise one or more images (e.g., image files), sequences of images, and/or videos (e.g., video files). Captured image data 426 may be associated with position data indicating a position of the subject of the image and/or a position of the drone or camera. The device control system 400 may further store and/or access additional sensor data from other sensor input devices 408, such as range information (e.g., from the drone or camera to an image subject), infrared imaging data, heat imaging data, temperature information, and/or ambient light intensity information, to name a few.

Position data 428 can include global positioning coordinates (e.g., indicating latitude, longitude, and/or altitude or elevation), street address information, and/or local coordinate information (e.g., one, two or three-dimensional locations in relation to the drone or camera).

A flight control module 432 may control movement of a drone, such as by controlling thrust, control surfaces or other flight control hardware 412.

An image capture module 434 may govern when and how to capture images (e.g., which subject to focus on, zoom level, type of imagery to capture (still versus video), and/or number of images to capture, to name a few.

An image identification module 436 or image classifier may perform image analysis, such as comparisons to reference images and/or reference data as described herein, to detect one or more subjects in a captured image, such as plant species, insect species, insect quantities, and/or other foreign objects.

An action module 438 may evaluate action logical rules with respect to captured and processed image data to determine one or more actions to take. The action module may also control one or more action devices (e.g., such as an action head and/or movable arm attached thereto) to cause them to carry out the determined actions.

Figure 5:
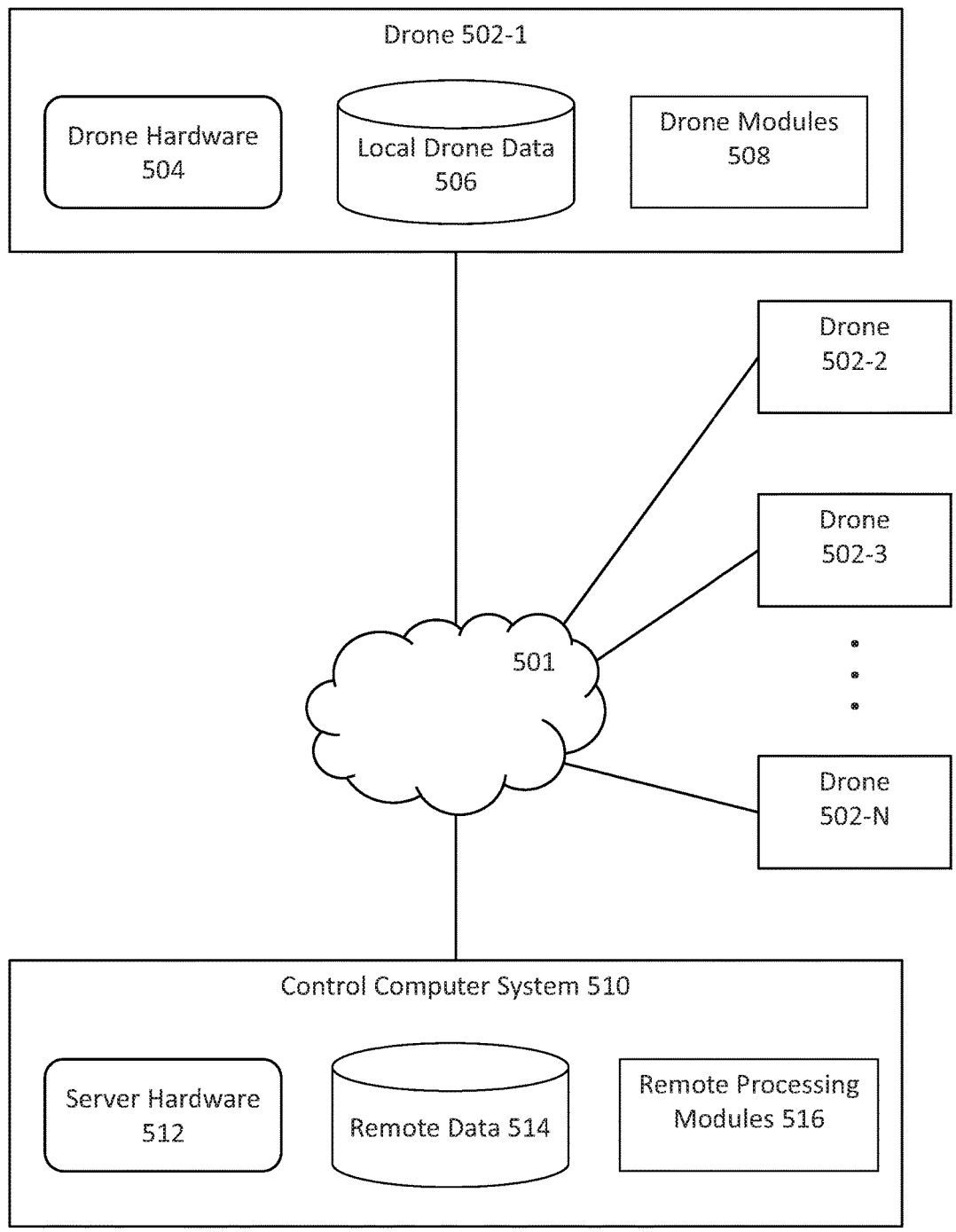
FIG. 5 is a schematic diagram of a drone scanning system according to an embodiment of the invention.

FIG. 5 shows a schematic diagram of an exemplary drone scanning system. The system can comprise one or more drones 502 (e.g., drones 502-1, 502-2, . . . 502-N) and/or a control computer system 510, which may be remotely located, such as on one or more servers. The devices (e.g., drones) and/or computer systems may be operatively connected directly, e.g., via wired or wireless communications, and/or indirectly, e.g., via a data network 501, such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In embodiments, any combination of communications channels may be utilized.

Processing of data from one or more drones 502 and/or control of each drone may be performed by one or more respective processors contained within or on each drone, one or more processors contained within or on one or more master drones that transmit commands to subordinate drones, and/or performed remotely such as at a remotely located control computer system, which may be one or more servers comprising one or more computers that receive data from and/or transmit instructions to the drones. In embodiments, any of the data processing and/or device control functions may be divided among entities, such as the drones 502 and remote control computer system 510. For example, flight controls or vehicle movement may be handled at each device, while image processing may be performed remotely. In embodiments, data acquisition may be handled at the device (e.g., capture of images and/or sensor data) and transmitted to the remotely located control computer system 510. The computer system 510 may process such data as described herein (e.g., perform image recognition and/or determine actions), and/or transmit instructions (e.g., action instructions, which may be machine-readable instructions to execute one or more determined actions) to the device 502 or to one or more other devices. Accordingly, one or more first drones 502 may acquire data while one or more second drones 502 may execute actions based upon determinations from the acquired data.

Both drones 502 and the control computer system 510 may include one or more processors, memory devices storing data in non-transitory computer-readable memory, which data may be organized in one or more databases, and communication portals (e.g., communications antennas and/or chipsets, as described herein). Drones and the control computer system may further comprise one or more input devices, e.g., to receive direct user input. Accordingly, drones may have keypads, touch screens, buttons with hardwired or programmed functionality, microphones, cameras (e.g., with gesture processing software), or other input devices. The control computer system 510 may include one or more input devices such as keyboards, mice, touchpads, touchscreens, microphones, cameras, to name a few, and/or output devices (e.g., display screens or speakers, to name a few).

Each drone 502 may also include the necessary respective hardware 504 (e.g., cameras, sensors, vehicle propulsion and control hardware), data 506 (e.g., rules for autonomous movement or control, flight path data, reference imagery and/or data, and/or captured data), and software modules 508 (e.g., any of the software modules described with respect to FIG. 4) to operate in such a divided control system.

Similarly, the control computer system 510 will include the necessary hardware 512 (e.g., processors, memory devices, and/or communication portals), data 514, and/or software modules 516 running on one or more processors to perform its assigned functions. Accordingly, remote data 514 can include databases of reference imagery and/or other reference data, which may be used in image analysis. Remote data 514 can also include a repository of captured images and/or other sensor data, such as from across time periods and/or from a plurality of drones. Remote processing modules 516 may include flight control modules, e.g., for controlling navigation routes or destinations, image analysis modules, and/or action modules to determine actions to take. The remote control computer system 510 may receive data from one or more drones, store such data, process such data, and/or generate and transmit machine-readable instructions to the drones.

It will be understood by those of ordinary skill in the art that one inventive device is an apparatus having image capturing capabilities and image recognition capabilities coupled with software that is programmed to determine whether or not an object in an image field is a pistil. A "pistil" herein is any physical, identifiable structure or shape of a plant part that is adapted to receive pollen. Once a pistil is detected, an automatic response in an action arm directs pollen to the identified pistil.

It will be understood that the device set forth herein may be programmed to provide an active response to remove, mitigate and/or react to various biological conditions. For example, in embodiments of the invention, the device may be programmed to detect a presence of skin conditions and send an alert or expel a marking material to a body site where a condition is identified. In an exemplary embodiment, the device is programmed to detect ticks embedded on user's skin by recognizing physical features consistent with ticks, such as appearance, color, size, shape etc.

The tick-detecting device may be disposed on movable platform, for example, as set forth herein, and programmed to move across an external aspect of a person or of a limb. In other embodiments, the device is a handheld unit that is grasped and manipulated by a user.

When a tick, bite, or mark is identified, the device automatically responds by directing the action head to the location of the detected tick and releases a blast of degradable ink, paint or similar marking material to designate a need for careful inspection or removal as the case may be.

In some embodiments of the invention, the device is programmable to be tailored to identified users for more specific tick detection. In this embodiment, the device is initially deployed to image the entire skin surface of a given user. The device detects all images that contrast with normal skin tone, and stores each of the images in a database (e.g. on a digital storage medium). Thus, after initial deployment, the system's database will have images of each mole, scar, or other dark marks on the user's skin. Upon subsequent deployment, the system will search for contrasting images and compare each contrasting image detected against the stored database. If a match is found, then the system will determine that the detected image was previously present on the user and no action is necessary. If, however, an image is detected for which there is no match—the system will then direct the action head to mark the newly found image. In this embodiment, a tick will present as an image for which there is no corresponding match, and it will trigger a response of the action head as set forth above.

Still in other embodiments of the invention, the device set forth herein may be programmed to provide an active response to remove, mitigate and/or react to various agricultural conditions.

For example, the device may be deployed in a field, garden, or orchard to detect early indications of weeds or similar harmful plants. The device may be provided on a stationary structure to scan an area of a field. Alternatively, the device may be mounted on a movable platform such as a robot, vehicle, or drone that is utilized to travel about a field and obtain images of plants growing therein. The software is programmed to distinguish between a weed and a desired crop or plant. When it detects any of various features associated with weeds or other undesired vegetation it will automatically react. In one embodiment, the device is trained to detect weeds by recognizing physical features such as appearance, color, size, shape etc. In the event that weeds are detected, the device automatically responds by directing the action arm to the detected weed or plant and releasing herbicide to the vicinity of the detected weeds.

Still in other embodiments of the invention, the device is configured to analyze images such as satellite or other aerial images of any of various terrains and identify features of interest. Features of interest may be any image segment that was not present in the same location in a previous version of the image, or it may be an image or image segment that the device is trained to recognize.

For example, in one embodiment of the invention, the device is configured to detect differences between a first image and a second image taken from the same location. In this embodiment, a first image (e.g. digital photograph) is captured of a first area (e.g. a geographical location) at a first time and is stored in the system memory. A second image of the same type as the first image is captured for the same location at a later time. The device then analyzes the second image and compares each segment to corresponding segments on the first image. If a difference is detected—the action arm automatically moves to the area on the second image where a difference was detected and expels a chalk or similar marking material, or it marks the area with a marking device such as marker pen affixed to the end of the action arm. It will be understood by those of ordinary skill in the art that "differences" may include the addition of new image areas, the removal of image areas or changes such as differences in color, texture, or the like.

The marking material may be stored as a liquid which may be sprayed by a nozzle on the action head. Alternatively, marking material may be stored as fine solid particles or liquid droplets, in air or other gas and which may be deposited by way of aerosol spraying by the action head.

In embodiments of the invention, the device is configured to only mark differences that are above a predetermined threshold value. For example, the device is configured to only react to changes that exceed a certain pixel count, pixel density, size, shape, color concentration, etc. as between a first image and an image acquired subsequently in time. That is, in embodiments of the invention, the tolerance for differences may be set by allowing the user to adjust the threshold for difference that warrant marking by the action head.

For example, in an aerial photograph that contains a tree, a user may want to note if the tree is removed. However, the user is uninterested in the tree's natural changes, such as, natural growth, leave shedding etc. In this regard, the device is configured to only mark changes that exceed a threshold. In this embodiment, in the event that a tree is added or removed, a sufficient number or concentration of pixels are involved so that the change amounts to a variation above the set threshold. As such, the system will automatically mark the area in the aerial photograph where the tree was added or removed. In other instances, a lower threshold of variation is desired. For example, in a security surveillance environment, a user may want to be alerted to even slight changes. In such environment, a user may set the tolerance to detect pixel changes associated with any object that is larger than a bird or a rodent.

In exemplary embodiments of the invention, images of archeological areas or cemeteries under threat of development or encroachment will be taken by a satellite or aerial camera at a first time period and stored on the system's memory. At a subsequent time (e.g. a week), a second set of images is taken of the same geographic location and the second set of images is compared to the first set of images stored in memory. Changes to the corresponding images will cause an instant marking response. This will enable the protection of sensitive and sacred areas known to be under threat. Extension to monitoring of forests against illegal logging, or to the protection of game preserves against poaching is evident.

It will be understood that the image substrate upon which the device is employed may be a physical printed image, such as a photograph or map, or it may be a digital image. It will be further understood that in embodiments of the invention any of various image types may be compared such as radar images, X-ray images, CT scan images and the like.

It will be understood by those of ordinary skill in the art that the system may be used to detect and mark differences between any two substrates. In embodiments of the invention, the system stores coordinates for each of the primary image (i.e. taken earlier in time) and the secondary images (i.e. images acquired later in time than a preceding image), such that it may compare the secondary image to the primary image at selected coordinates. Alternatively, the system is trained to match image features of one image with image features of a second image without storing coordinates.

In other embodiments of the invention, the device is configured to automatically detect differences in printed or written matter, such as handwritten Torah scrolls. In embodiments of the invention, an image of a reference scroll is stored in the device's memory. The device is configured to analyze a second scroll with respect to the reference scroll. In embodiments of the invention, the device is configured to move in an x and y direction and image each letter in each row on each page or section of the scroll. For each letter, the device performs a comparison with a corresponding letter on the reference scroll stored in memory. If a difference is detected, the action head is automatically directed to the area on the secondary image where the difference was detected and it expels a marking material in the area of the identified difference.

In embodiments of the invention, a comparison between letters of the reference scroll and second scroll include a checklist of image characteristics. For example, when detecting an "aleph," (first letter of Hebrew alpha bet), the device is configured to check whether or not the corresponding aleph on the second scroll has an upper segment, a lower segment, a diagonal segment and connecting segments. To the extent that any of these image segments are missing, or unconnected the device will automatically mark the second scroll. The device is also configured to detect areas within a letter that may be missing ink. For example, the device is configured to magnify each letter and determine its outside perimeter. Thereafter, the system scans areas within the perimeter that have a sharp contrast from dark to light. In embodiments, the system is configured to only detect areas of contrast that are smaller than a predetermined threshold. This allows the system to mark only areas of missing ink or areas of cracked ink, but it will not mark a letter having an open center. Such marking will, thus, notify a user as to at least any one of an insertion, deletion or misformation of a letter.

It should be understood that the preferred embodiment was described to provide the best illustration of the principles of the invention and its practical application to thereby enable one of ordinary skill in the art to utilize the invention in various embodiments and with various modifications as are suited to the particular use contemplated.

What is claimed is:

1. A unitary device for detecting and automatically neutralizing offending objects, comprising:
    an image capturing device;
    an image recognition system connected to the image capturing device, the image recognition system being trained to recognize characteristics of plants, the image recognition system being further trained to recognize offending objects;
    a moveable arm provided on the unitary device, the moveable arm deployable to contact an offending object;
    an action head provided on the moveable arm; and
    software configured to detect a presence of an offending object and to automatically command the moveable arm to move the action head to the offending object when the presence of an offending object is detected.

2. The device of claim 1, whereby the offending object is a weed.

3. The device of claim 2, wherein the image recognition system is trained to recognize any of a color, shape, or size of the weed.

4. The device of claim 2, wherein the movable arm is configured to release herbicide in the vicinity of the weed.

5. The device of claim 2, wherein the action head comprises a gripping device.

6. The device of claim 5, wherein the gripping device is configured to grip the weed.

7. The device of claim 1, wherein the offending object is an insect.

8. The device of claim 1, wherein the offending object is a swarm of insects.

9. The device of claim 8, wherein the movable action head is configured to release marking material onto the plant or tree.

10. The device of claim 1, wherein the offending object is a hole in a plant or tree formed by one or more insects.

* * * * *